United States Patent
Manzke et al.

(10) Patent No.: US 9,625,254 B2
(45) Date of Patent: Apr. 18, 2017

(54) INTEGRATION OF FIBER OPTIC SHAPE SENSING WITHIN AN INTERVENTIONAL ENVIRONMENT

(75) Inventors: Robert Manzke, Sleepy Hollow, NY (US); Raymond Chan, San Diego, CA (US); Gert Wim 'T Hooft, Eindhoven (NL); Adrien Emmanuel Desjardins, Waterloo (CA); Bharat Ramachandran, Morganville, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 439 days.

(21) Appl. No.: 13/980,905

(22) PCT Filed: Jan. 23, 2012

(86) PCT No.: PCT/IB2012/050296
§ 371 (c)(1),
(2), (4) Date: Jul. 22, 2013

(87) PCT Pub. No.: WO2012/101563
PCT Pub. Date: Aug. 2, 2012

(65) Prior Publication Data
US 2013/0308137 A1 Nov. 21, 2013

Related U.S. Application Data

(60) Provisional application No. 61/436,704, filed on Jan. 27, 2011.

(51) Int. Cl.
*A61B 5/00* (2006.01)
*G01B 11/24* (2006.01)
(Continued)

(52) U.S. Cl.
CPC ........... *G01B 11/24* (2013.01); *A61B 34/20* (2016.02); *G01B 11/18* (2013.01); *A61B 2034/2061* (2016.02); *A61B 2034/2072* (2016.02)

(58) Field of Classification Search
CPC ...... A61B 2019/5261; A61B 5/05; A61B 5/00
(Continued)

(56) References Cited

U.S. PATENT DOCUMENTS 4,750,487 A * 6/1988 Zanetti .......................... 606/130
5,957,844 A   9/1999 Dekel et al.
(Continued)

FOREIGN PATENT DOCUMENTS

| EP | 1901107 | 3/2008 |
| JP | S6486930 A | 9/1987 |
| WO | WO2011100124 | 8/2011 |

*Primary Examiner* — Joel Lamprecht

(57) ABSTRACT

An integrated optical shape sensing system and method include an arrangement structure (132) configured to receive a fiber port or connector. A platform (130) is configured to provide a distance relationship with the arrangement structure such that the fiber port or connector is trackable to provide a location reference. The platform secures a patient in proximity to the arrangement structure. An optical shape sensing enabled interventional instrument (102) has a first optical fiber cable connectable to the fiber port or connector. An optical interrogation module (108) is configured to collect optical feedback from the instrument and has a second optical fiber cable connectable to the fiber port or connector such that a known reference position is provided for accurate shape reconstruction.

21 Claims, 5 Drawing Sheets

(51) Int. Cl.
*G01B 11/16* (2006.01)
*A61B 34/20* (2016.01)

(58) Field of Classification Search
USPC .................................. 600/424, 182; 606/130
See application file for complete search history.

(56) References Cited

U.S. PATENT DOCUMENTS

| | | |
|---|---|---|
| 6,845,190 B1 | 1/2005 | Smithwick et al. |
| 7,123,790 B2 | 10/2006 | Rosman et al. |
| 8,439,826 B2 | 5/2013 | Onoda et al. |
| 2004/0165810 A1* | 8/2004 | Fujita ............................... 385/12 |
| 2005/0259919 A1 | 11/2005 | Aldridge et al. |
| 2007/0197896 A1* | 8/2007 | Moll et al. .................... 600/407 |
| 2008/0245946 A1* | 10/2008 | Yu ................................. 248/637 |
| 2009/0137952 A1 | 5/2009 | Ramamurthy et al. |
| 2010/0030063 A1 | 2/2010 | Lee et al. |
| 2011/0054199 A1 | 3/2011 | Taha et al. |

* cited by examiner

INTEGRATION OF FIBER OPTIC SHAPE SENSING WITHIN AN INTERVENTIONAL ENVIRONMENT

This disclosure relates to medical devices and methods, and more particularly to systems and methods for integrating optical shape sensing structures into an interventional environment for reliable and flexible usage during a medical procedure.

Shape sensing based on fiber optics equates to distributed strain measurement in optical fibers with characteristic Rayleigh scatter patterns. Rayleigh scatter occurs as a result of random fluctuations of the index of refraction in the fiber core, inherent to the fiber manufacturing process. These random fluctuations can also be modeled as a Bragg grating with a random variation of amplitude and phase along the grating length. If strain or temperature change is applied to the optical fiber, the characteristic Rayleigh scatter pattern changes. An optical measurement can be performed first with no strain/temperature stimulus applied to the fiber to produce a reference scatter pattern and then again after induction of strain/temperature. Cross-correlation of the Rayleigh scatter spectra of the fiber in the strained/unstrained states determines the spectral shift resulting from the applied strain. This wavelength $\Delta\lambda$ or frequency shift $\Delta v$ of the backscattered pattern due to temperature change $\Delta T$ or strain along the fiber axis $\epsilon$ is very similar to the response of a fiber Bragg grating:

$$\frac{\Delta\lambda}{\lambda} = -\frac{\Delta v}{v} = K_T \Delta T + K_\varepsilon \varepsilon,$$

where the temperature coefficient $K_T$ is the sum of the thermal expansion and thermo-optic coefficient. The strain coefficient $K_\epsilon$ is a function of group index, n, the components of the strain optic tensor, $p_{i,j}$, and Poisson's ratio:

$$K_\varepsilon = 1 - \frac{n_{eff}^2}{2(p_{12} - v(p_{11} + p_{12}))}.$$

Thus, a shift in temperature or strain is merely a linear scaling of the spectral wavelength shift $\Delta\lambda$.

Optical Frequency Domain Reflectometry (OFDR) essentially performs frequency encoding of spatial locations along the fiber which enables distributed sensing of local Rayleigh reflection patterns. In OFDR, the laser wavelength or optical frequency is linearly modulated over time. For coherent detection, the backscattered wave is mixed with a coherence reference wave at the detector. The detector receives a modulated signal owing to the change of constructive to destructive interference and vice versa while scanning the wavelength. Its frequency $\Omega$ marks the position s on the fiber and its amplitude is proportional to the local backscattering factor and the total amplitude attenuation factor of forward plus backward propagation through the distance s. By performing a Fourier transform of the detector signal using, for example, a spectrum analyzer, this method permits for simultaneous recovery of the backscattered waves from all points s along the fiber. Thus, strain on different portions of the fiber can be determined by measuring spectral shifts of the characteristic Rayleigh scattering pattern using any number of shift-detection or pattern-matching methods (e.g. block-matching with cross-correlation or other similarity metric, computation of signal phase change, etc.) in combination with OFDR.

A shape sensing device can be built using the above distributed strain measurement methodology when either two or more optical fibers are in a known spatial relationship such as when integrated in a multi-core shape sensing fiber. Based on a reference shape or location with reference Rayleigh scatter patterns (or reference strains) new shapes can be reconstructed using relative strains between fibers in a known/given/fixed spatial relationship.

Several parameters are considered when designing a distributed strain measurement system based on OFDR and Rayleigh scatter interrogation which forms the basis of many optical shape sensing prototype systems. Given the following equations one can calculate the sample size $\Delta s$, the maximum fiber length $L_{max}$ and the number of samples to be acquired $N_{max}$:

$$\Delta s \cong \frac{\lambda_s \lambda_f}{2n\Delta\lambda}, \; L_{max} \cong \frac{R_s \lambda_s \lambda_f}{4n\frac{\partial \lambda}{\partial t}}, \; N_{max} \cong \frac{R_s \Delta\lambda}{\frac{\partial \lambda}{\partial t}},$$

where $\lambda_{s,f}$ is the start/final wavelength, n is the group index, $R_s$ is the sampling rate and $$\frac{\partial \lambda}{\partial t}$$

is the sweep frequency.

The coherence length of the source during a sweep should be larger than $2*n*L_{max}$. This gives an upper limit to the line width $\delta v = c/(2*n*L_{max})$. The lasers may have a line width below 10 MHz corresponding to a coherence length larger than 10 m. For reasonable tether lengths of 1-2 m the coherence length is more than sufficient. A tether is a length of fiber connected to the medical instrument. A patch cord connects the instrument to an interrogation unit.

In practice, $L_{max}$ will be taken to be larger than the tether length to accommodate for a reasonable amount of patch cord between interrogation unit and tether. The minimum size of the fiber length sets an upper limit to the wavelength step. Keeping the same number of 10 m for the maximum fiber length gives a maximum step size in wavelength of about 0.040 pm. Note that when an application needs to have a larger distance than 10 m between console and tether, one can always increase the length of the reference arm in the interferometer. This reference arm fiber length should, however, not exceed the length of the patch cord connected to the tether.

The step size determines the accuracy of the optical clock which monitors the wavelength sweep. The free spectral range of such a clock should not exceed a few hundred times, say 300, the minimum step size, since phase measurements better than a degree are hard to ensure. In the example above, this would mean that the free spectral range of the clock should not exceed 12 pm. This sets a limit to the wavelength repeatability of the laser from one sweep to the next. If the laser does not fulfill this requirement, one is forced to calibrate every sweep with a known standard (e.g., the absorption lines of a low pressure HCN cell). This would influence the refresh rate of the interrogation system in a negative way.

To have as fast a data processing scheme as possible, a number of data points to a power of 2 should be taken and the sweep should not be linear in wavelength but linear in wave vector (the inverse of the wavelength). This permits time-optimized fast Fourier transforms. The deviation from linearity is determined by the tether length. For 1 m, this would mean that the deviations from linearity should be less than 100 MHz. There are no lasers that fulfill this requirement, and resampling the data is necessary.

Shape reconstruction can be performed in an iterative manner: $\vec{r}_{i+1} = \vec{r}_i + \Delta \vec{s}_i$, where $\vec{r}_i$ is the position vector to the ith spatial element along the shape sensing fiber and $\Delta \vec{s}_i$ is the reconstructed incremental step vector derived from the actual strain measurement of the multi-core fiber. For shape reconstruction one can assume $\vec{r}_0$ to be $(0,0,0)^T$ or any other given point, i.e., a reference point from a fixture with known relation to the (X-ray) imager. Any error acquired in $\Delta \vec{s}_i$, for example, due to measurement noise, propagates forward and impacts the shape reconstruction accuracy.

In accordance with the present principles, an integrated optical shape sensing system and method include an arrangement structure configured to receive a fiber port or connector. A platform is configured to provide a distance relationship with the arrangement structure such that the fiber port or connector is trackable to provide a location reference. The platform secures a patient in proximity to the arrangement structure. An optical shape sensing enabled interventional instrument has a first optical fiber cable connectable to the fiber port or connector. An optical interrogation module is configured to collect optical feedback from the instrument and has a second optical fiber cable connectable to the fiber port or connector such that a known reference position is provided for accurate shape reconstruction.

An integrated optical shape sensing system includes an arrangement structure configured to receive one or more fiber ports or connectors such that the one or more fiber ports or connectors are trackable to provide a location reference. A table is configured to receive the arrangement structure. An optical shape sensing enabled interventional instrument has a first optical fiber cable connectable to the one or more fiber ports or connectors. An optical interrogation module is configured to collect optical feedback from the instrument and has a second optical fiber cable connectable to the one or more fiber ports or connectors such that the one or more fiber ports or connectors provide a known reference position for accurate shape reconstruction. One or more imaging devices is/are configured to image the interventional instrument using the location reference for image registration.

A method includes providing an integrated optical shape sensing system having an arrangement structure configured to receive one or more fiber ports or connectors such that the one or more fiber ports or connectors are trackable to provide a location reference, a platform configured to provide one or more distance relationships with the arrangement structure, an optical shape sensing enabled interventional instrument having a first optical fiber cable connectable to the one or more fiber ports or connectors and an optical interrogation module configured to collect optical feedback from the instrument and having a second optical fiber cable connectable to the one or more fiber ports or connectors such that the one or more fiber ports or connectors provide a known reference position for accurate shape reconstruction; connecting the first and second optical cables to at least one of the fiber ports or connectors; securing at least a portion of the patient in proximity to the arrangement structure; and shape sensing the instrument by employing a position of the at least one of the fiber ports or connectors as a reference.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
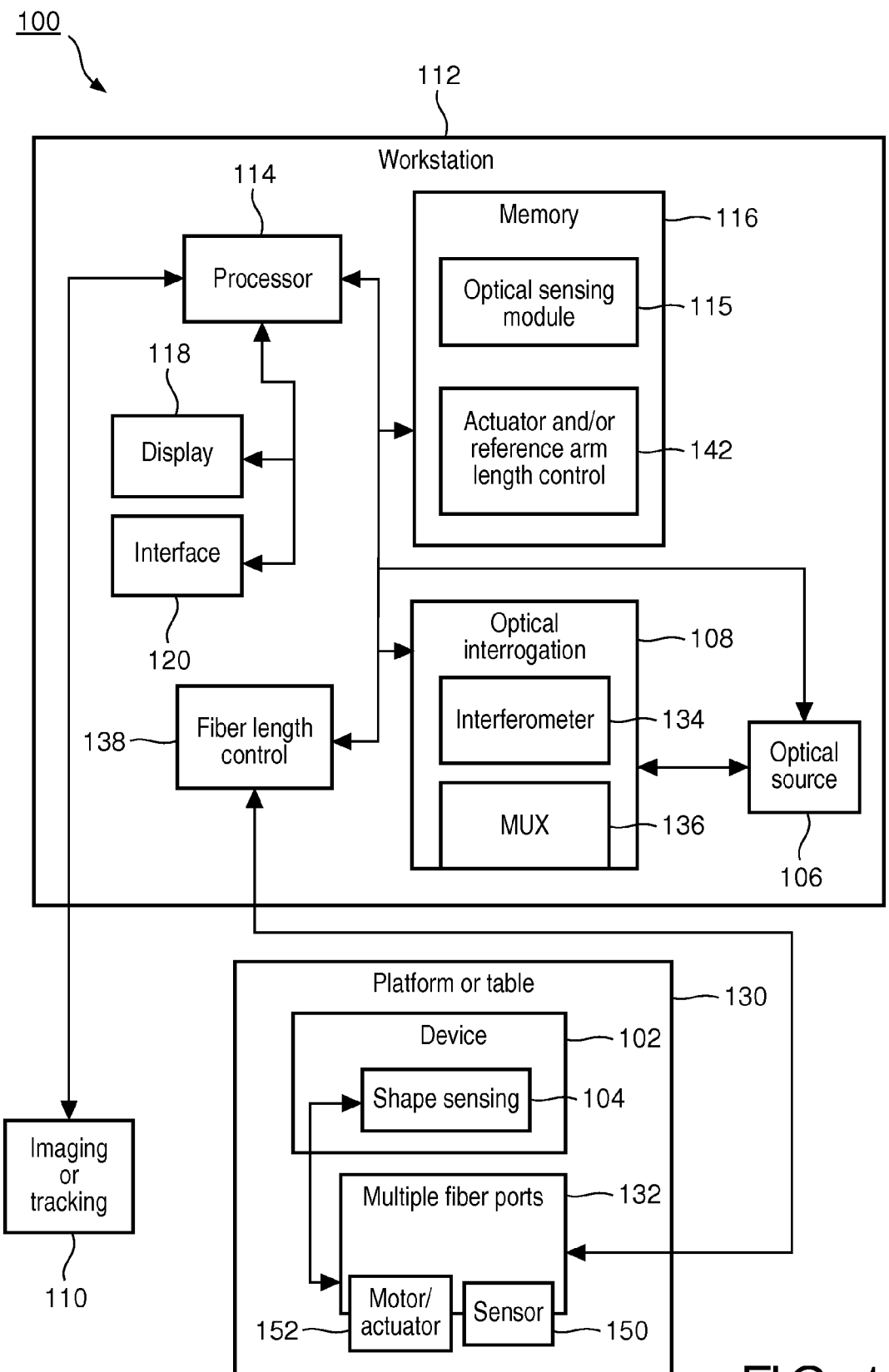
FIG. 1 is a block/flow diagram showing a system/method having integrated shape sensing for an interventional or clinical setting in accordance with the present principles.

In accordance with the present principles, deployment of optical shape sensing within an interventional environment or laboratory needs specific arrangements of connectors, consoles, and shape sensing fiber configurations (e.g., lengths, attachment geometries, etc.) within the clinical setting to optimize both tracking functionality and workflow. Multiple parameters influence the utility of shape sensing within the interventional environment. In accordance with the present principles, arrangements and structures for deploying optical shape sensing within a clinic are provided. The arrangements may be employed in interventional lab settings; multimodality setups; full integration of optical shape sensing systems into clinical imaging setups, etc.

In one embodiment, for integration of fiber optic shape sensing (OSS) systems in an interventional X-ray suite, several aspects need to be considered. For example, the fiber has to be launched from known reference positions to permit accurate shape reconstruction. Such locations need to be known with respect to the imaging system to permit direct registration. In addition, parameters such as bandwidth of the interrogation laser, sweep rate, coherence length, sampling rate, fiber length, etc. need to be selected and optimized depending on the integration with the imaging system.

In particularly useful embodiments, methods which permit optimal deployment of a shape sensing system within an interventional suite are provided. Based on clinical criteria, arrangements are provided for OSS fiber connection (e.g., along the side of the patient) which ensure proper fiber launching references. Those arrangements also permit straight-forward registration with imaging equipment such as X-ray, Ultrasound, etc.

It also should be understood that the present invention will be described in terms of medical instruments; however, the teachings of the present invention are much broader and are applicable to any instruments employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Referring now to the drawings in which like numerals represent the same or similar elements and initially to FIG. 1, a system 100 for performing a medical procedure in an interventional setting which employs integrated optical sensing structures is illustratively depicted. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from a shape sensing device 104. Optical sensing module 115 is configured to use the optical signal feedback (and any other feedback, e.g., electromagnetic (EM)) to reconstruct deformations, deflections and other changes associated with a medical device 102 and/or its surrounding region. The medical device 102 may include a catheter, a guidewire, a probe, an endoscope, a robot or other active device, etc.

Workstation 112 may include a display 118 for viewing internal images of a subject if an imaging or tracking system 110 is employed. The imaging system 110 may include, e.g., a magnetic resonance imaging (MRI) system, a fluoroscopy system (X-Ray), a computed tomography (CT) system, an ultrasonic (US) system, positron emission tomography (PET), single photon emission computed tomography (SPECT), etc. Tracking may include electromagnetic tracking, US, etc. Display 118 may also permit a user to interact with the workstation 112 and its components and functions. This is further facilitated by an interface 120 which may include a keyboard, mouse, a joystick or any other peripheral or control to permit user interaction with the workstation 112.

Workstation 112 includes an optical source 106 to provide optical fibers with light. An optical interrogation unit or module 108 is employed to control light to/from all fibers. This permits the determination of strains or other parameters, which will be used to interpret the shape, orientation, etc. of the interventional device 102. The light signals will be employed as feedback to make adjustments, to access errors and to calibrate the device 102 or system 100.

Shape sensing device 104 includes one or more fibers which are configured to exploit their geometry for detection and correction/calibration of shape tracking errors. Optical interrogation module 108 works with optical sensing module 115 (e.g., shape determination program) to permit tracking of instrument or device 102. The optical fibers of shape sensing device 104 may be attached to the instrument 102 in a known or predetermined geometry to permit interrogation of tracking errors and calibration.

The shape sensing (OSS) system 104 provides Rayleigh scattering for an accurate determination of a scatter pattern and fiber geometry information (e.g., helical pitch) from preset positions. Based on clinical criteria related to application requirements and ease of use, one or more arrangements 132 for OSS fiber connections or fiber ports are provided. In one embodiment, the fiber ports 132 are disposed at a position corresponding to a lateral position of a patient. The fiber port positions 132 may be along side a patient within a table or platform 130 or within calibration frames or other structure affixed in proximity to the patient. The ports 132 ensure fiber launching reference behavior that is either fixed and therefore known, or reconfigurable but measurable and constrained for optimal estimation of fiber shape based on defined boundary conditions. Such arrangements permit straight-forward registration with imaging equipment such as X-ray, ultrasound, etc.

The fiber port positions 132 are located to optimize fiber length between tethers to the OSS device 102 and patch cords between the tether and the optical interrogation unit 108. In addition, positions of the connectors or ports 132 are trackable or known. This feature permits knowledge of an exact reference or fiber launching position to enable registration with the imaging or tracking system 110. The tracking can be performed using position encoders or sensors 150 attached to the connectors or ports 132. The fiber port positions 132 may be motorized using an actuator or motor 152 and monitored so that the movement of the arrangement or individuals ports/connectors can be known at all times.

The optical interrogation unit 108 includes one or more interferometers 134, which include a reference arm length. In one embodiment, a reference arm length of the interferometer 134 of the interrogation unit 108 includes preset lengths or includes semi or fully-automated control of the reference arm length based on patient size, procedure type, and system configuration positions. Based on this information, hardware/software optimization may be implemented by a control module 142 that would trade-off known parameters of influence, e.g., sweep frequency, wavelength range, wavelength step width, coherence length, reference arm for maximum length and resolution of shape sensing activated fiber.

The optical sensing module 115 may have the ability to store different reference arm lengths based on the patient length and preset positions 132 of the patient table. Each fiber optic connector location (132) could have a different reference arm length based on its position (near patient's feet, sliding or hanging) that maximizes the sample points along the fiber's length. This also can overcome any limitation of losing data by increasing a fiber offset value, and potentially reduces the length of the shape sensing fiber needed.

The interrogation unit 108 may further include an optoelectronic multiplexer 136 which permits interrogation of multiple fiber arms to track catheters, devices, ultrasound transducers, which are physically in different locations but connected to the same interrogation unit 108.

A fiber optic length control unit 138 may be provided in the workstation 112 (backplane) or integrated into the patient table 130 for reduction of fiber length. Different fiber lengths may be selectable to optimize the configuration. In one embodiment, the optical interrogation module 108 with optical components and detection electronics may be a separate unit and mounted at the workstation or at a closer position such as attached to the patient table, e.g., within a pedestal mount, or within a table mounted docking station for the interrogation unit 108. Optionally, a table-mounted or bedside display 118 and user-interface 120 may be provided for improving usability of the configuration.

Figure 2A:
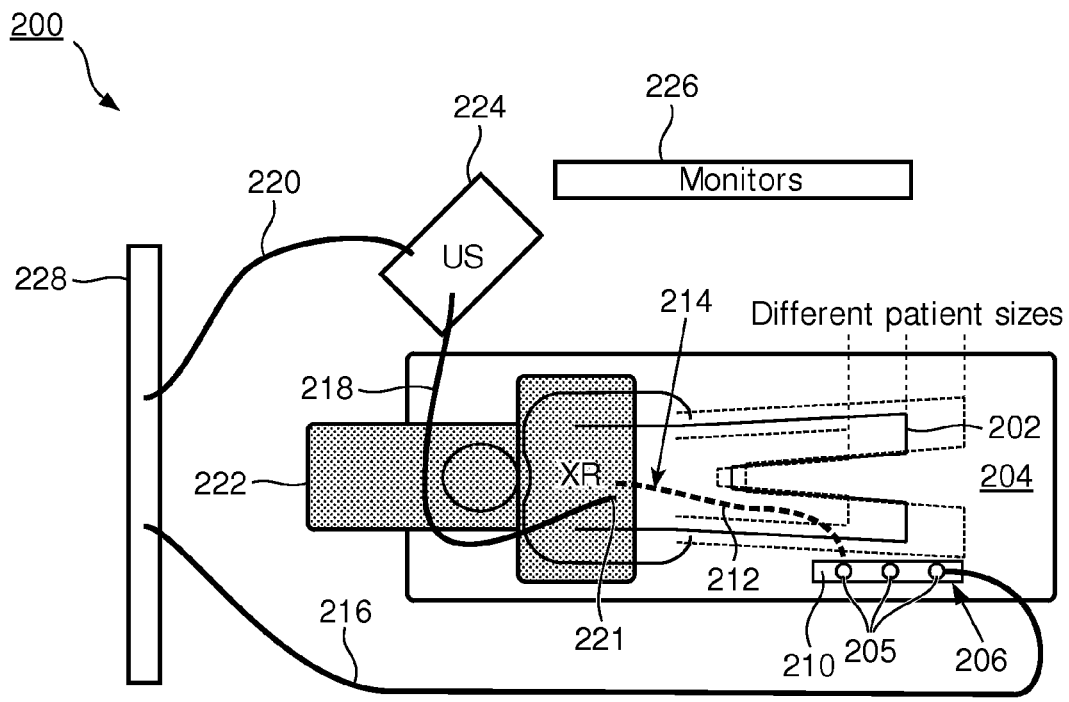
FIGS. 2A and 2B shows a top and side view respectively of a system having integrated shape sensing with an arrangement structure or configuration for connecting fiber optics in the interventional or clinical setting in accordance with the present principles.
Figure 2B:
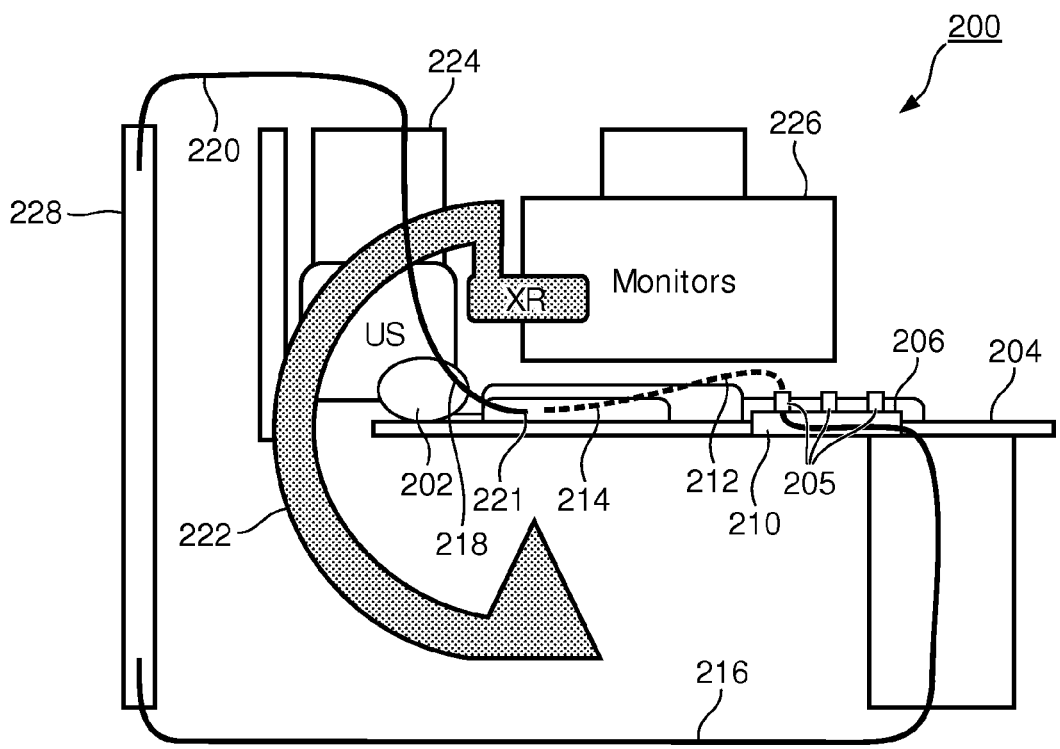

Referring to FIGS. 2A and 2B, FIG. 2A shows a top view and FIG. 2B shows a side view of an interventional setting 200 configured in accordance with the present principles. A patient 202 is depicted on a platform or table 204. The table 204 includes a multi-core optical shape sensing fiber connector arrangement 206 with docking ports 205 in close proximity to access points or positions relative to the patient 202. The docking ports 205 may be, for example, at the level of the femoral or brachial access points which are common access positions, at the side of the patient thorax for liver oncology applications, etc. In this embodiment, the docking ports 205 are fixed within the table 204 or within table-mounted supports 210.

The docking ports 205 are positioned at plurality of locations to permit adjustment based upon the height or size of the patient 202. The ports 205 are configured with standard or advanced fiber optic connecters to permit easy connection/disconnection, accounting for the specifics of dedicated shape sensing fiber. The connectors may include ST connection technology or the like.

On the patient side, a fiber optic cable 212 connects to an interventional device 214 with optical fiber shape sensing capabilities. The cable 212 connects to a docking port 205. Another fiber optic cable 216 connects to an opposite side of the docking port 205 to complete the connection with an interrogation unit 228 (which may be part of a workstation 112).

In this example, another interventional device 221 is employed for use with an illustrative imaging device 224, which in this example includes an ultrasonic imaging system (224). The imaging system 224 may employ the device 221 with fiber optic shape sensing capability. A cable 218 connects to the device 221 and is coupled to the imaging system 224 at a predetermined position which is further connected to the interrogation unit 228 by a fiber optic cable 220. Cables 218 and 220 are connected in a predetermined configuration with system 224, but may also be routed through the arrangement 206 as described.

An X-ray machine 222 may be employed to track or image the devices 221 and 214. Imaging and other information may be viewed on monitors/displays 226. The display images may be registered to the shape sensed data using the position of the ports 205 as a reference.

Figure 3:
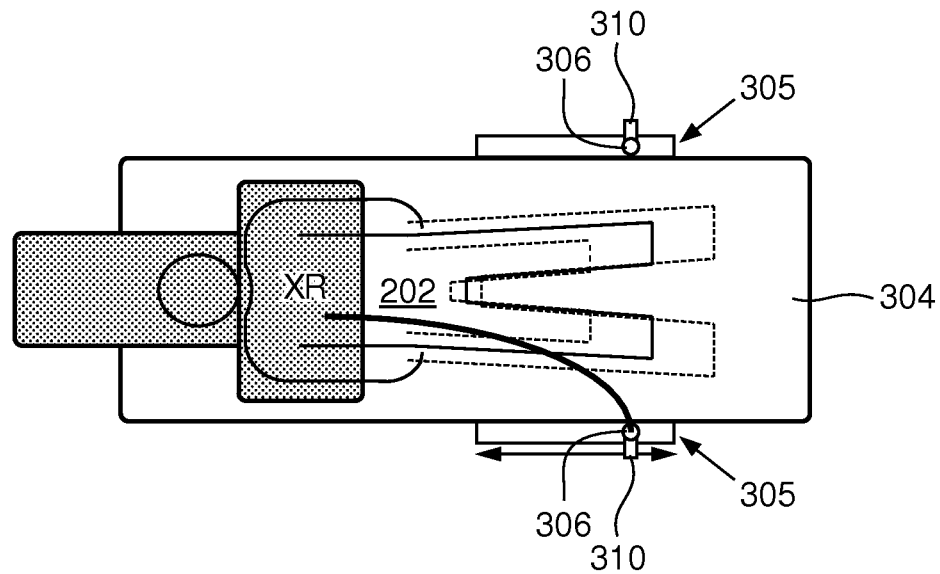
FIG. 3 shows a top view of a system having the arrangement structure or configuration with adjustable fiber connectors in accordance with one illustrative embodiment.

Referring to FIG. 3, another arrangement 305 is depicted for ports 306. In this embodiment, sliding fiber optic connectors 306 are slideably engaged within the arrangement 305 to permit positional adjustment (e.g., in a track securable with a set screw or other mechanisms). The sliding fiber optic connectors 306 may be disposed along sides of a table 304 to be available at appropriate positions relative to the patient 202. The arrangement 305 may be configured within the table 304 or on table-mounted supports (305).

In one embodiment, connectors 306 slide within the arrangement 305 and can be latched or locked into preset positions by a securing mechanism 310 to provide known launching points for shape reconstruction. The securing mechanism 310 may include a screw, lever, snap, detect or other mechanical structure to secure a position of the connectors 306.

Sliding connectors 306 may have radio-opaque markers or other imaging visible markers for simultaneous image-based characterization of a fiber reference configuration. In this way, the configuration and connector positions can be determined directly by the imaging system(s).

The connectors 306 may be automatically actuated for self-positioning based on procedure requirements and/or are positionally tracked to provide feedback about reference fiber configurations. In addition, connectors 306 may be fixed or actuated using a position sensor (150, FIG. 1) for registration with another system, e.g., X-ray system registration, movement of the patient, movement of the table, etc. Preset position actuation may employ either a semi-automated or fully-automated motorized setup (e.g., using control module 142 and actuators 152, FIG. 1).

The connectors 306 are preferably configured in all embodiments to assure a smooth curvature at launching points to provide constrained boundary conditions for shape reconstruction. For example, the fiber optic cables coming from the connectors 306 should have bend limiters to ensure that a radius of curvature is appropriately maintained.

Figure 4:
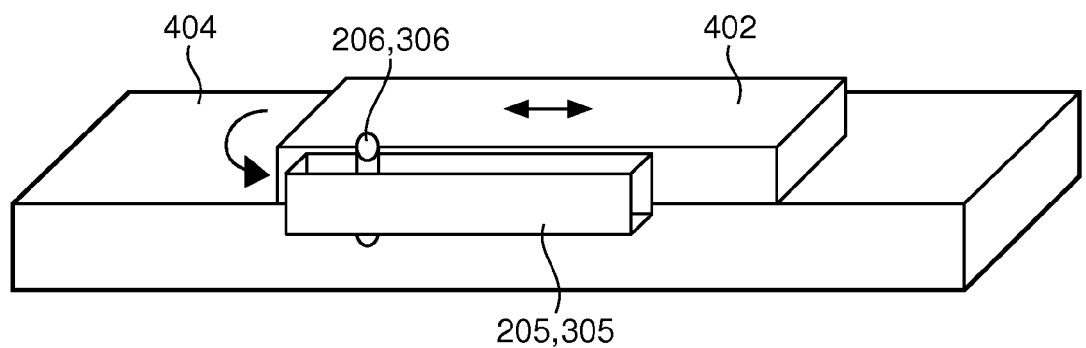
FIG. 4 shows a perspective view of an adjustable pad having arrangement configurations with adjustable fiber connectors in accordance with one illustrative embodiment.

Referring to FIG. 4, a fiber launching pad 402 may be embedded within a table top or be reconfigurable and moved (manually or automatically) into various table positions depending on patient positioning, procedure type, anatomy targeted, and access desired. The pad 402 may be positioned on a table 404 and secured thereto. The pad 402 includes an arrangement 205 or 305 to permit fiber ports 206 or connectors 306 to be configurable therein. The pad 402 may be adjusted using actuators or manual repositioning as needed.

Figure 5:
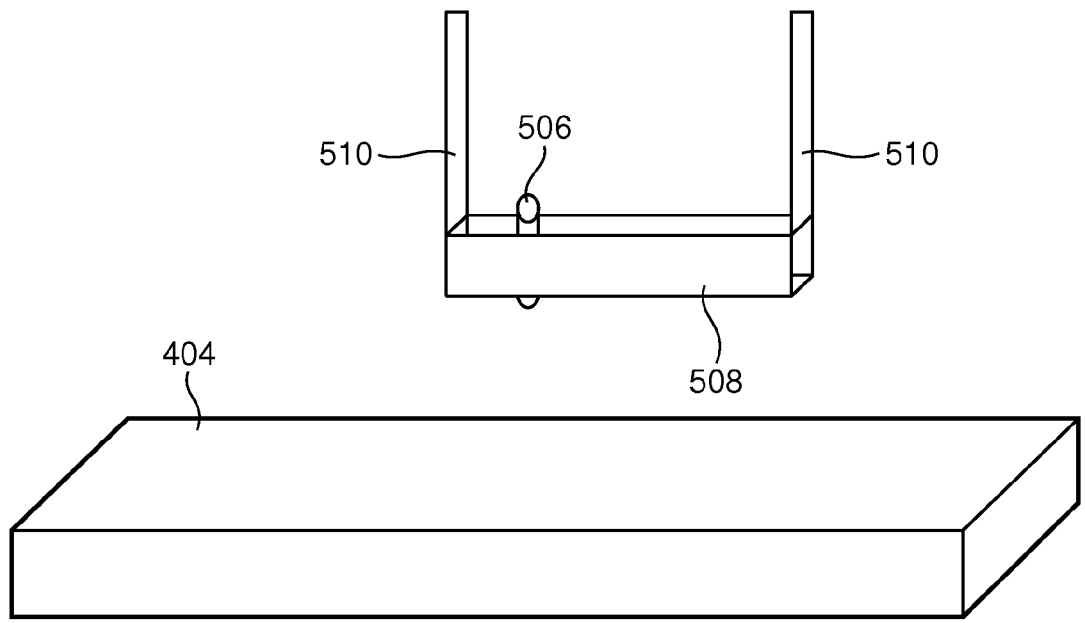
FIG. 5 shows a perspective view of a system having an arrangement structure or configuration with an adjustable fiber connector wall or ceiling mounted in accordance with one illustrative embodiment.

Referring to FIG. 5, fiber optic connectors 506 may be placed on other structures or arrangements 508. In the example depicted in FIG. 5, the arrangement 508 includes an overhead rail or similar mount 510 suspended, e.g., from a ceiling or wall. The mount 510 includes preset positions registered with the geometry of other systems, e.g., an X-ray machine, etc., to permit clearance for other equipment. The preset positions locate ports or connectors 506 for fiber connections.

Figure 6:
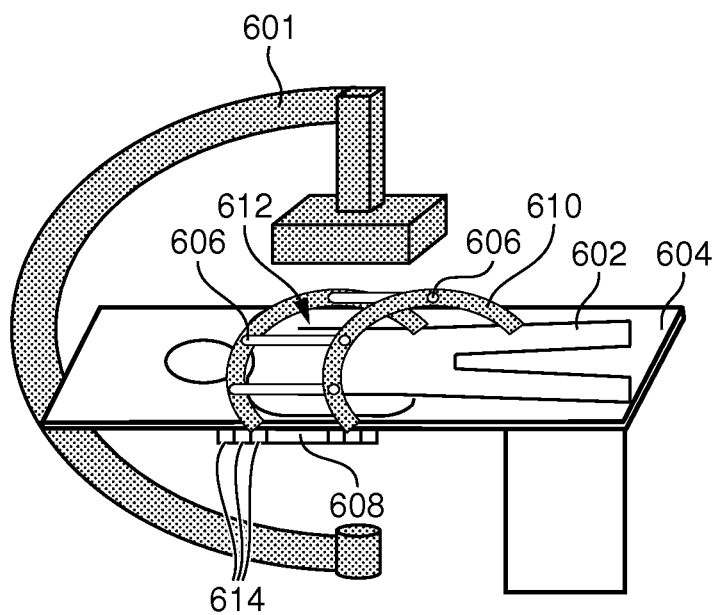
FIG. 6 shows a perspective view of a system having arrangement structure or configuration with adjustable fiber connectors mounted on a three-dimensional structure in accordance with another illustrative embodiment.

Referring to FIG. 6, a mounting 608 includes preset positions 614 on a table 604 for mounting a three-dimensional structure 610 over the patient 602. The structure 610 may provide X-ray imaging of an X-ray machine 601 or other processing through openings 612 in an unobstructed fashion. The structure 610 is preferably configured to offer multiple known launching points 606 close to the point of entry into the patient. Windows or openings 612 may be automatically or manually actuated to positions that are optimal for a given procedure or anatomy of interest. Preset position actuation may employ either a semi-automated or fully-automated motorized setup.

Figure 7:
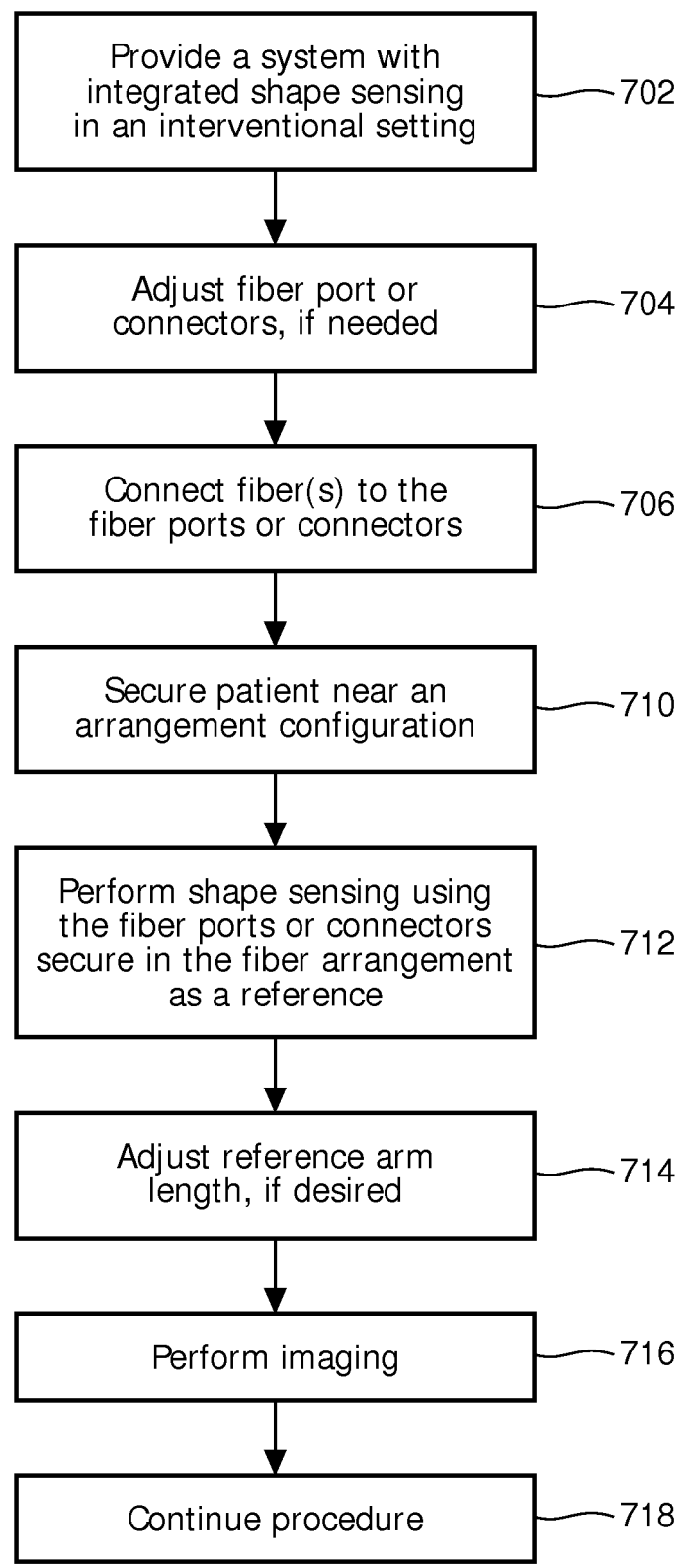
FIG. 7 is a block/flow diagram showing a method for integrating and employing shape sensing in an interventional or clinical setting in accordance with one embodiment.

Referring to FIG. 7, a block flow/diagram shows a method for integrating and employing a shape sensing instrument in an interventional environment in accordance with an illustrative embodiment. In block 702, an integrated optical shape sensing system is provided. The system includes an arrangement structure configured to receive one or more fiber ports or connectors, and a platform configured to provide one or more distance relationships with the arrangement structure. An optical shape sensing enabled interventional instrument has a first optical fiber cable connectable to the one or more fiber ports or connectors, and an optical interrogation module is configured to collect optical feedback from the instrument. The optical interrogation module has a second optical fiber cable connectable to the one or more fiber ports or connectors such that the one or more fiber ports or connectors provide a known reference position for accurate shape reconstruction. The arrangement structure may include configurations with slidable connectors, three-dimensional structures adjustably connected to the platform to permit the one or more fiber ports or connectors to be positioned over the patient, wall or ceiling mounted arrangement structures, etc.

In block 704, the one or more fiber ports or connectors may be adjusted in the arrangement configuration in accordance with at least one of a patient size and a procedure type. In block 706, the first and second optical cables are connected to at least one of the fiber ports or connectors. In block 710, at least a portion of the patient is secured in proximity to the arrangement structure. Blocks 706 and 710 are interchangeable and either may be performed before the other. In block 712, the instrument is shape sensed by employing a position of the at least one of the fiber ports or connectors as a reference. This step may be performed at anytime during the procedure. In block 714, a reference arm length of an interferometer may be adjusted in accordance with at least one of patient size, procedure type and system configuration. In block 716, imaging is performed. This may be performed throughout the procedure, and may employ the fiber ports or connections as reference positions. In block 718, the procedure continues.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for systems and methods for integration of fiber optic shape sensing within an interventional environment (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An integrated optical shape sensing system, comprising:
   an arrangement structure configured to receive one or more fiber ports or connectors;
   a platform configured to provide one or more distance relationships with the arrangement structure, the platform for securing at least a portion of the patient in proximity to the arrangement structure such that the one or more fiber ports or connectors are trackable to provide a location reference;
   an optical shape sensing enabled interventional instrument having a first optical fiber cable connectable to the one or more fiber ports or connectors; and
   an optical interrogation module configured to collect optical feedback from the instrument and having a second optical fiber cable connectable to the one or more fiber ports or connectors such that the one or more fiber ports or connectors provide a known reference position for accurate shape reconstruction.

2. The system as recited in claim 1, wherein the arrangement structure is connected to at least one side of the platform.

3. The system as recited in claim 2, wherein the one or more fiber ports or connectors are adjustable in the arrangement structure.

4. The system as recited in claim 2, wherein the one or more fiber ports or connectors are adjusted in accordance with at least one of a patient size and a procedure type.

5. The system as recited in claim 1, wherein the arrangement structure includes a three-dimensional structure adjustably connected to the platform to permit the one or more fiber ports or connectors to be positioned over the platform.

6. The system as recited in claim 5, wherein the three-dimensional structure includes windows for imaging a patient on the platform.

7. The system as recited in claim 1, wherein the platform includes a moveable pad that includes the arrangement structure.

8. The system as recited in claim 1, wherein the arrangement structure is wall-mounted or ceiling mounted.

9. The system as recited in claim 1, further comprising a reference arm length control module configured to adjust a reference arm length of an interferometer in accordance with at least one of patient size, procedure type and system configuration.

10. An integrated optical shape sensing system, comprising:
an arrangement structure configured to receive one or more fiber ports or connectors such that the one or more fiber ports or connectors are trackable to provide a location reference;
a table configured to receive the arrangement structure;
an optical shape sensing enabled interventional instrument having a first optical fiber cable connectable to the one or more fiber ports or connectors;
an optical interrogation module configured to collect optical feedback from the instrument and having a second optical fiber cable connectable to the one or more fiber ports or connectors such that the one or more fiber ports or connectors provide a known reference position for accurate shape reconstruction; and
one or more imaging devices configured to image the interventional instrument using the location reference for image registration.

11. The system as recited in claim 10, wherein the arrangement structure is connected to at least one side of the table.

12. The system as recited in claim 11, wherein the one or more fiber ports or connectors are adjustable in the arrangement structure.

13. The system as recited in claim 11, wherein the one or more fiber ports or connectors are adjusted in accordance with at least one of a patient size and a procedure type.

14. The system as recited in claim 10, wherein the arrangement structure includes a three-dimensional structure adjustably connected to the table to permit the one or more fiber ports or connectors to be positioned over the table.

15. The system as recited in claim 14, wherein the three-dimensional structure includes windows for imaging a patient on the table.

16. The system as recited in claim 10, further comprising a reference arm length control module configured to adjust a reference arm length of an interferometer in accordance with at least one of patient size, procedure type and system configuration.

17. The system as recited in claim 10, wherein the one or more fiber ports or connectors include visible markers to permit registration between the imaging system and the instrument.

18. A method, comprising:
providing an integrated optical shape sensing system having an arrangement structure configured to receive one or more fiber ports or connectors such that the one or more fiber ports or connectors are trackable to provide a location reference, a platform configured to provide one or more distance relationships with the arrangement structure, an optical shape sensing enabled interventional instrument having a first optical fiber cable connectable to the one or more fiber ports or connectors and an optical interrogation module configured to collect optical feedback from the instrument and having a second optical fiber cable connectable to the one or more fiber ports or connectors such that the one or more fiber ports or connectors provide a known reference position for accurate shape reconstruction;
connecting the first and second optical cables to at least one of the fiber ports or connectors;
securing at least a portion of the patient in proximity to the arrangement structure; and
shape sensing the instrument by employing a position of the at least one of the fiber ports or connectors as a reference.

19. The method as recited in claim 18, wherein the one or more fiber ports or connectors are adjustable in the arrangement configuration in accordance with at least one of a patient size and a procedure type.

20. The method as recited in claim 18, wherein the arrangement structure includes a three-dimensional structure adjustably connected to the platform to permit the one or more fiber ports or connectors to be positioned over the platform and the method further comprising imaging a patient on the table through a window in the three-dimensional structure.

21. The system as recited in claim 18, further comprising adjusting a reference arm length of an interferometer in accordance with at least one of patient size, procedure type and system configuration.

* * * * *